US010689650B2

(12) United States Patent
Yoneyama et al.

(10) Patent No.: US 10,689,650 B2
(45) Date of Patent: Jun. 23, 2020

(54) METHOD OF FIXING AND EXPRESSING PHYSIOLOGICALLY ACTIVE SUBSTANCE

(71) Applicants: STELIC INSTITUTE & CO., Tokyo (JP); (NATIONAL UNIVERSITY CORPORATION) NIIGATA UNIVERSITY, Niigata (JP)

(72) Inventors: Hiroyuki Yoneyama, Tokyo (JP); Kenji Suzuki, Niigata (JP)

(73) Assignees: STELIC INSTITUTE & CO., Tokyo (JP); (NATIONAL UNIVERSITY CORPORATION) NIIGATA UNIVERSITY, Niigata (JP)

( * ) Notice: Subject to any disclaimer, the term of this patent is extended or adjusted under 35 U.S.C. 154(b) by 0 days.

(21) Appl. No.: 16/269,359

(22) Filed: Feb. 6, 2019

(65) Prior Publication Data

US 2019/0153447 A1    May 23, 2019

Related U.S. Application Data

(63) Continuation of application No. 15/241,830, filed on Aug. 19, 2016, now abandoned, which is a continuation of application No. 14/158,607, filed on Jan. 17, 2014, now abandoned, which is a continuation of application No. 12/666,983, filed as application No. PCT/JP2008/061709 on Jun. 27, 2008, now abandoned.

(30) Foreign Application Priority Data

Jun. 29, 2007    (JP) ................. 2007-171361

(51) Int. Cl.
| | | |
|---|---|---|
| C07H 21/04 | (2006.01) |
| C12N 15/113 | (2010.01) |
| A61K 9/00 | (2006.01) |
| A61K 9/08 | (2006.01) |
| A61K 9/10 | (2006.01) |
| A61K 31/396 | (2006.01) |
| A61K 31/7088 | (2006.01) |
| A61K 31/7105 | (2006.01) |
| A61K 48/00 | (2006.01) |
| A61P 9/10 | (2006.01) |
| A61P 1/00 | (2006.01) |
| A61P 17/02 | (2006.01) |
| A61P 19/02 | (2006.01) |
| A61K 31/713 | (2006.01) |

(52) U.S. Cl.
CPC .......... *C12N 15/113* (2013.01); *A61K 9/0019* (2013.01); *A61K 9/0024* (2013.01); *A61K 9/0053* (2013.01); *A61K 9/08* (2013.01); *A61K 9/10* (2013.01); *A61K 31/396* (2013.01); *A61K 31/7088* (2013.01); *A61K 31/713* (2013.01); *A61K 31/7105* (2013.01); *A61K 48/0075* (2013.01); *A61P 1/00* (2018.01); *A61P 9/10* (2018.01); *A61P 17/02* (2018.01); *A61P 19/02* (2018.01)

(58) Field of Classification Search
None
See application file for complete search history.

(56) References Cited

U.S. PATENT DOCUMENTS

| | | |
|---|---|---|
| 4,054,352 A | 10/1977 | Rudin |
| 6,464,998 B1 | 10/2002 | Beuzard et al. |
| 7,008,626 B2 | 3/2006 | Ishikawa et al. |
| 7,381,419 B2 | 6/2008 | Oku et al. |
| 2003/0105061 A1 | 6/2003 | Ishikawa et al. |
| 2003/0143732 A1 | 7/2003 | Fosnaugh et al. |
| 2003/0191070 A1 | 10/2003 | Oku et al. |
| 2004/0120970 A1 | 6/2004 | Jacobs et al. |
| 2004/0241843 A1 | 12/2004 | Baker et al. |
| 2004/0259247 A1 | 12/2004 | Tuschl et al. |
| 2004/0265230 A1 | 12/2004 | Martinez et al. |
| 2005/0013854 A1 | 1/2005 | Mannino et al. |

(Continued)

FOREIGN PATENT DOCUMENTS

| | | |
|---|---|---|
| JP | 9-505575 | 6/1997 |
| JP | 2003-516365 | 5/2003 |

(Continued)

OTHER PUBLICATIONS

Krebs et al. ("Localized, targeted, and sustained siRNA delivery." Chemistry—A European Journal 17.11 (2011): 3054-3062.*

(Continued)

*Primary Examiner* — Kimberly Chong
(74) *Attorney, Agent, or Firm* — Oblon, McClelland, Maier & Neustadt, L.L.P.

(57) ABSTRACT

The present invention provides methods for retaining and expressing physiologically active substances in a target tissue-specific-manner, by administering the physiologically active substances to target submucous tissue. Specifically, the present inventors demonstrated that, when physiologically active substances were directly administered into submucous tissues without using a carrier, the physiologically active substances were effectively and safely retained at the administration sites over long periods without loss and diffusion, and produced the effect acting in a reservoir-like fashion. The physiologically active substances administered as described above were demonstrated to produce the therapeutic effect without having an influence on organs other than the administered organ.

8 Claims, 10 Drawing Sheets
Specification includes a Sequence Listing.

(56) References Cited

U.S. PATENT DOCUMENTS

| | | | |
|---|---|---|---|
| 2005/0106729 A1 | 5/2005 | Rosenblatt et al. | |
| 2005/0164964 A1 | 7/2005 | Artursson et al. | |
| 2005/0232927 A1 | 10/2005 | Clarke | |
| 2005/0272682 A1* | 12/2005 | Evers | C12N 15/111 514/44 A |
| 2006/0105991 A1 | 5/2006 | Ishikawa et al. | |
| 2006/0128659 A1 | 6/2006 | Habuchi et al. | |
| 2006/0217656 A1* | 9/2006 | Freyman | A61M 37/0069 604/31 |
| 2006/0286073 A1 | 12/2006 | Tolentino et al. | |
| 2007/0198048 A1* | 8/2007 | Behan | A61F 2/04 606/194 |
| 2007/0224208 A1 | 9/2007 | Guo et al. | |
| 2007/0258952 A1 | 11/2007 | Tong et al. | |
| 2008/0085242 A1 | 4/2008 | Artursson et al. | |
| 2009/0060892 A1 | 3/2009 | Yoneyama et al. | |
| 2009/0182136 A1 | 7/2009 | Wengel et al. | |
| 2009/0202515 A1 | 8/2009 | Yoneyama et al. | |
| 2009/0275634 A1 | 11/2009 | Hazum et al. | |
| 2009/0325899 A1 | 12/2009 | Ishikawa et al. | |
| 2010/0028350 A1 | 2/2010 | Jevnikar et al. | |
| 2011/0275891 A1 | 11/2011 | Sheml | |

FOREIGN PATENT DOCUMENTS

| | | |
|---|---|---|
| JP | 2005-503199 | 2/2005 |
| JP | 2005-538943 | 12/2005 |
| JP | 2007/0502616 A | 2/2007 |
| WO | 01/41810 | 6/2001 |
| WO | 01/93856 | 12/2001 |
| WO | 02/102436 | 12/2002 |
| WO | 2005/063293 | 7/2005 |
| WO | 2007/049424 | 5/2007 |
| WO | 2007/119498 | 5/2007 |
| WO | 2008/029493 | 3/2008 |

OTHER PUBLICATIONS

Rychahou, P. G., et al. "RNAi directed to the PI3K p85α subunit attenuates inflammatory changes associated with DSS-induced colitis." Journal of Surgical Research 130.2 (2006): 199.*

Baumgart, Daniel C., and Simon R. Carding. "Inflammatory bowel disease: cause and immunobiology." The Lancet 369.9573 (2007): 1627-1640.*

Takehara et al., "In Vivo Gene Transfer and Expression in Rat Stomach by Submucosal Injection of Plasmid DNA" Human Gene Therapy (Mar. 1996) 7:589-593.

Luo et al. (Int. J. Exp. Path. 2009, 90: 558-274).

Wolff et al. (Gene Therapy 2003: 453-458).

A manual entitled "Medical Products4 Orthopedic Article Approval No. 16100BZZ01355000 Specifically controlled medical devices Soft tissue injected agents using collagen" (attached to commodity of) KOKEN Atelocollagen Implant (Syringe-type) Published Mar. 1, 2005.

Abarinejad et al., "Colony-Stimulating Factor-1 Blockade by Antisense Oligonucleotides and Small Interfering RNAs Suppresses Growth of Human Mammary Tumor Xenografts in Mice" Cancer Research, 64:5378-5384 (Aug. 1, 2004).

Akamo et al., "Chemotherapy Targeting Regional Lymph Nodes by Gastric Submucosal Injection of Liposomal Adriamycin in Patients with Gastric Carcinoma" Jpn J Cancer Res. (Jun. 1994) 85(6):652-8 (see International Search Report).

Bass, Brenda L. "The Short Answer" Nature (2001) 411 :428-9.

Bennett et al. "Adenovirus Vector-Mediated In Vivo Gene Transfer Into Adult Murine Retina" Opthal. Visual Sci (Apr. 1994) 35(5):2535-2542.

Bhavsar et al, "Polymeric nano- and microparticle technologies for oral gene delivery" Expert Opinion Drug Delivery (May 2007) 4(3):197-213.

Cejka et al., "Short interfering RNA (siRNA): took or therapeutic?" Clinical Science, 110:47-58 (2006).

Cristofaro et al., "Sirna therapy of inflammatory bowel disease {IBD)" Gastroenterology, {Apr. 2006), 130{4) Supp 2):A343.

Harimoto, "Methods of In Vivo Gene Transfer into Bladder without Viral Vectors" The Journal of the Osaka City Medical Center (1999) 48(3-4):435-42 (See the International Search Report).

International Search Report from PCT/JP2008/061709 dated Aug. 5, 2008.

Kawauchi et al., Digestive Organ and Immunology {2006) 43:98-101 See the International Search Report at line #7 for explanation).

Stedman's Medical Dictionary, Lippinkott, Williams and Wilson, http://www_medilexicon.com/medicaldictionary.php? =58990 (Jul. 16, 2013).

Suzuki, Ensyousei Cyou Shikkan no Kakkiteki Chiryouhou ni Kansuru Rinsyou Kenkyu Heisei 15-17nendo Sougou Kenkyu Houkokusyo (2006) 31-4 {See the International Search Report).

Suzuki, Ensyousei Cyou Shikkan no Kakkiteki Chiryouhou ni Kansuru Rinsyou Kenkyu Heisei 17nendo Soukatsu Rinsyou Kenkyu Houkokusyo (2006) 14-5 (See the International Search Report).

Suzuki, Ensyousei Cyou Shikkan no Kakkiteki Chiryouhou ni Kansuru Rinsyou Kenkyu Heisei 18nendo Soukatsu Buntan Kenkyu Houkokusyo (2007) 16-9 (See the International Search Report).

Takehara et al., "In Vivo Gene Transfer and Expression in Rat Stomach by Submucosal Injection of Plasmid DNA" Human Gene Therapy (Mar. 20, 1996) 7:589-593.

Takehara et al., "Gene transfer into gastrointestinal tract by submucosal injection of naked DNA" Gastroenterology 1996) 110(4)(Supp):A1124.

Ohtake et al., "Human N-Acetylgalactosamine 4-Sulfate 6-0-Sulfotransferase cDNA is Related to Human B Cell Recombination Activating Gene-associated Gene" The Journal of Biological Chemistry (Nov. 23, 2001) 276 (47): 43894-43900.

Http:/www.webmd.com/digestive-disorders/pictu re-of-the-colon (May 17, 2014).

Vickers et al., "Efficient Reduction of Target RNAs by Small Interfering RNA and RNase H-dependent Antisense Agents" Journal of Biological Chemistry (Feb. 2003) 289(9):7108-7118.

Herweijer and Wolff, "Progress and prospects: naked DNA gene transfer and therapy" Gene Therapy (2003)10:453-458.

* cited by examiner

SEQUENCE LISTING

<160> NUMBER OF SEQ ID NOS: 6

<210> SEQ ID NO 1
<211> LENGTH: 27
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (26)..(27)
<223> OTHER INFORMATION: overhang

<400> SEQUENCE: 1
ggagcagagc aagaugaaua caaucag                                27

<210> SEQ ID NO 2
<211> LENGTH: 27
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (26)..(27)
<223> OTHER INFORMATION: overhang

<400> SEQUENCE: 2
gauuguauuc aucuugcucu gcuccau                                27

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
gtgagttctg ctgcggtcca                                        20

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
agtccatgct gatgcccaga g                                      21

<210> SEQ ID NO 5
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 5
ctgccaagta tgacatca                                          18

<210> SEQ ID NO 6
<211> LENGTH: 21
<212> TYPE: DNA

```
<213> ORGANISM: Artificial Sequence
<220> FEATURE:
<223> OTHER INFORMATION: synthetic oligonucleotide

<400> SEQUENCE: 6
tactccttgg aggccatgta g                                              21
```

METHOD OF FIXING AND EXPRESSING PHYSIOLOGICALLY ACTIVE SUBSTANCE

TECHNICAL FIELD

The present invention relates to methods for retaining and expressing physiologically active substances in a target tissue-specific manner, in which the physiologically active substances are administered to the target submucous tissue.

BACKGROUND ART

At the nonclinical experiment level, it is now becoming possible to treat disease-model animals using techniques of introducing genes of interest, or conversely, suppressing the expression of genes of interest through RNA interference. In the case of "nucleic acid pharmaceutical agents" using such a gene or an siRNA (generally termed "nucleic acid"), the nucleic acid administered to the living body needs to continuously produce its effect and be retained over a long period. A critical factor in achieving the therapeutic effect of nucleic acid pharmaceutical agents is how the drug delivery system (DDS) is designed.

Meanwhile, when nucleic acids are administered to the body as is, they are rapidly degraded and thus fail to work. Accordingly, such nucleic acids are usually administered by using a carrier such as a viral vector, liposome, or atelocollagen as a DDS.

However, nucleic acid pharmaceutical agents have a serious disadvantage in that the carrier itself may induce an adverse immune response or such in the body and thus not only the nucleic acid but also carrier must be assessed for its influence on the body. For example, according to a report, atelocollagen, when used as a carrier, induces a hypersensitive immune reaction to calf dermis derived collagen; the instruction manual (Non-patent Document 1) attached to the product named Koken Atelocollagen implant (syringe type) describes that adverse effects were clinically found in 24 of a total of 1,192 patients.

Another problem is that, even when a carrier is used, normally, the introduced nucleic acid can only be retained for about one week.

Prior art documents include, for example, Patent Documents 1 to 7 listed below. However, all of these inventions use carriers. Thus, the above-described problems still remain unsolved.

[Patent Document 1] Japanese Patent Application Kohyo Publication No. (JP-A) 2003-516365 (unexamined Japanese national phase publication corresponding to a non-Japanese international publication)
[Patent Document 2] JP-A (Kohyo) 2005-538943
[Patent Document 3] JP-A (Kohyo) H09-505575
[Patent Document 4] Japanese Patent Application Saikohyo Publication No. (JP-A) WO01-093856 (unexamined Japanese national phase publication corresponding to a Japanese international publication
[Patent Document 5] JP-A (Kohyo) 2005-503199
[Patent Document 6] Japanese Patent Application Kokai Publication No. (JP-A) 2007-119498 (unexamined, published Japanese patent application)
[Patent Document 7] (Granted/Registered) Japanese Patent No. 4054352
[Non-patent Document 1] Instruction manual attached to the product named Koken Atelocollagen implant (syringe type)

DISCLOSURE OF THE INVENTION

Problems to be Solved by the Invention

The present invention provides methods for locally retaining and expressing physiologically active substances at the administration site. Specifically, the present invention provides methods for retaining and expressing physiologically active substances in a target tissue-specific manner, in which the physiologically active substances are administered to target submucous tissue.

Means for Solving the Problems

The present inventors conducted dedicated studies to solve the above-described issues. Specifically, as a method of solving the above problems, the present inventors evaluated establishment of a novel method that produces effects of physiologically active substances without using carriers.

Specifically, the present inventors conducted an experiment of injecting nucleic acids, which are an embodiment of the physiologically active substances, into the submucous tissue of the large intestine in experimental animals such as rats, and evaluated the effect. Common knowledge envisaged that the solution would be rapidly lost due to diffusion or degradation. However, the present inventors obtained an unpredictable result. When the present inventors actually injected solutions containing nucleic acids into submucous tissues, the injected solutions were retained at the administration site without diffusing and produced effects acting as a reservoir. This suggests that the submucous microenvironment is very special and the living body functions like a carrier by utilizing its own environment. Such a phenomenon has not been observed with previous intramuscular, intravascular, or intramucosal delivery methods, and thus is specific to the submucous microenvironment. Specifically, the present invention discovered that the living body itself had sites that function as a DDS. The present inventors thus succeeded in establishing the novel concept of "nature's DDS" and a novel method based on it.

The submucous tissue of the intestinal tract has been shown to be much more effective than other matrices, for example, when pancreatic Langerhans islets are cultured in vitro (Tian X H et al. Hepatobiliary Pancreat Dis Int. 4: 524, 2005). Even this shows that submucous tissues have a very special microenvironment. In particular, the submucous pH, sugar chains, and cell composition are assumed to create an environment that is very suitable for maintaining nucleic acids.

Furthermore, the present inventors injected iopamidol, India ink, or siRNA, each of which is an embodiment of the physiologically active substances, into the submucous tissue of the large intestine in rats and mice. The result showed that every substance was selectively retained at the injection sites in the submucous tissue of the large intestine.

The present inventors discovered that, when siRNA was administered into the submucous tissue of colitis model mice, the increase in expression of the GalNAc4S-6ST gene in the large intestine was significantly suppressed while it had no influence on other normal organs. In addition, it was also revealed that the suppression of GalNAc4S-6ST gene expression in the large intestine resulted in suppression of inflammatory activity and thus strong suppression of intestinal fibrous degeneration. Furthermore, the histological therapeutic effect was also demonstrated based on the finding that the administration significantly suppresses epithelial disruption, infiltration of inflammatory cells into lamina propria and submucosa, and thickening of muscular layer in the large intestinal tissue.

As described above, the present invention demonstrated that, when nucleic acids are administered endoscopically into the submucous tissues of the large intestine of subjects, the nucleic acids were specifically retained at the administration site over a long period and could continuously produce their effect. The present invention also enables physiologically active substances to produce their effects without assistance of a carrier, and thus has solved the previous problem associated with the use of carriers.

The present invention relates to methods for retaining and expressing physiologically active substances in a tissue-specific manner, in which the physiologically active substances are administered to the submucous tissue, and more specifically,

[1] a method for retaining and expressing a physiologically active substance in a target submucous tissue-specific manner, wherein the physiologically active substance is administered into the submucous tissue;

[2] the method of [1], wherein the physiologically active substance is selected from nucleic acids, proteins, carbohydrates, lipids, or low-molecular-weight compounds;

[3] the method of [2], wherein the nucleic acid is an siRNA; and

[4] the method of any one of [1] to [3], wherein the physiologically active substance is administered in combination with a pharmaceutically acceptable carrier.

The present invention also provides:

[5] a method for treating or preventing a disease, which comprises the step of retaining and expressing a physiologically active substance in a submucous tissue-specific manner, by administering the physiologically active substance to the diseased submucous tissue.

Effects of the Invention

The present invention provides a Drug Delivery System (DDS) for maintaining a physiologically active substance (for example, a nucleic acid, protein, carbohydrate, lipid, low-molecular-weight compound, etc.) in a target submucous tissue over a long period, for continuously producing a physiologically active substance useful to the living body, or for continuously removing a physiologically active substance that is harmful to the living body. The present invention enables safe and effective retention of physiologically active substances at the administration sites over long periods without assistance of a carrier. Thus, physiologically active substances can be retained without considering side effects of carriers as before. This significantly increases the clinical feasibility of pharmaceutical agents using physiologically active substances (for example, nucleic acid pharmaceutical agents). In addition, the above-described pharmaceutical agents have very little systemic side effects, because they specifically produce their effects at the injection sites. Thus, the pharmaceutical agents are much safer than conventional methods.

Endoscopic examination (of the esophagus, stomach, and small and large intestines) is routinely carried when diagnosing gastrointestinal diseases. Thus, the present invention has the advantage in that physiologically active substances (for example, nucleic acids) can be injected (for treatment) at the same time as diagnosis. The present invention is also expected to be applicable to the submucous tissues of the nose, subconjunctival tissue, or such, and thus enables actual clinical use of pharmaceuticals for cranial nerve diseases or ophthalmic diseases, in which physiologically active substances have been difficult to deliver in the past. Thus the methods of the present invention have a superior effect than the conventional local administration methods, specifically, enemas, nasal drips, and ocular instillations.

A: an image of the submucous tissue of the large intestine; B: an image observed under a fluorescence microscope after FITC staining; C: an image obtained by superimposing A with B.

Figure 2:
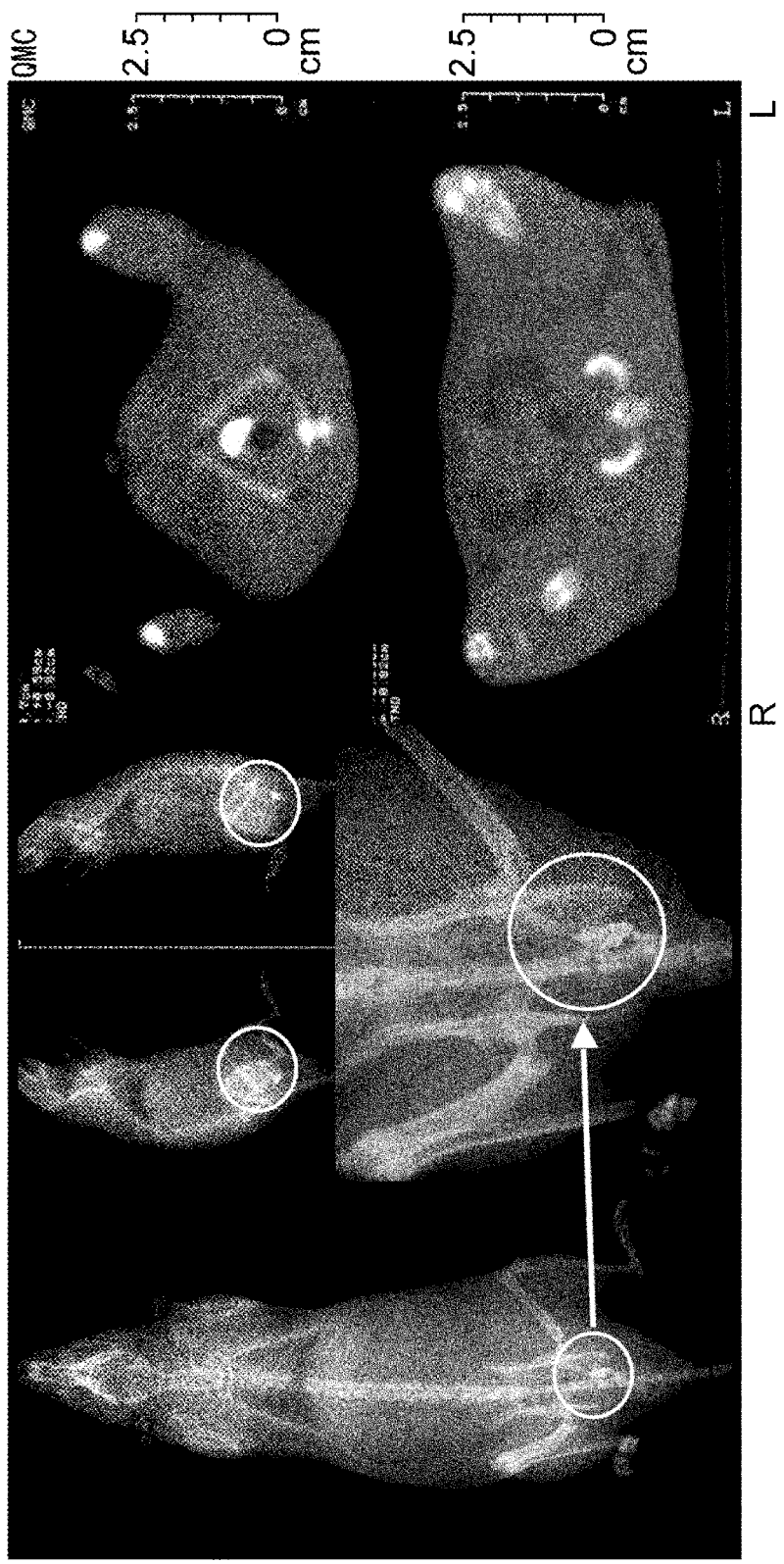

FIG. 2: photographs showing retention of a substance administered into the submucous tissue of the large intestine in normal rats. An X-ray finding showed that iopamidol (white; within circle) was retained at a specific site within the large intestine (left). In this figure, the upper panels show lateral view images, and the bottom panel shows a magnified image. A CT finding (right) showed that iopamidol was retained at the injection site on the ventral side of large intestine (upper panel) but it was undetectable on the craniad slice (lower panel).

Figure 3:
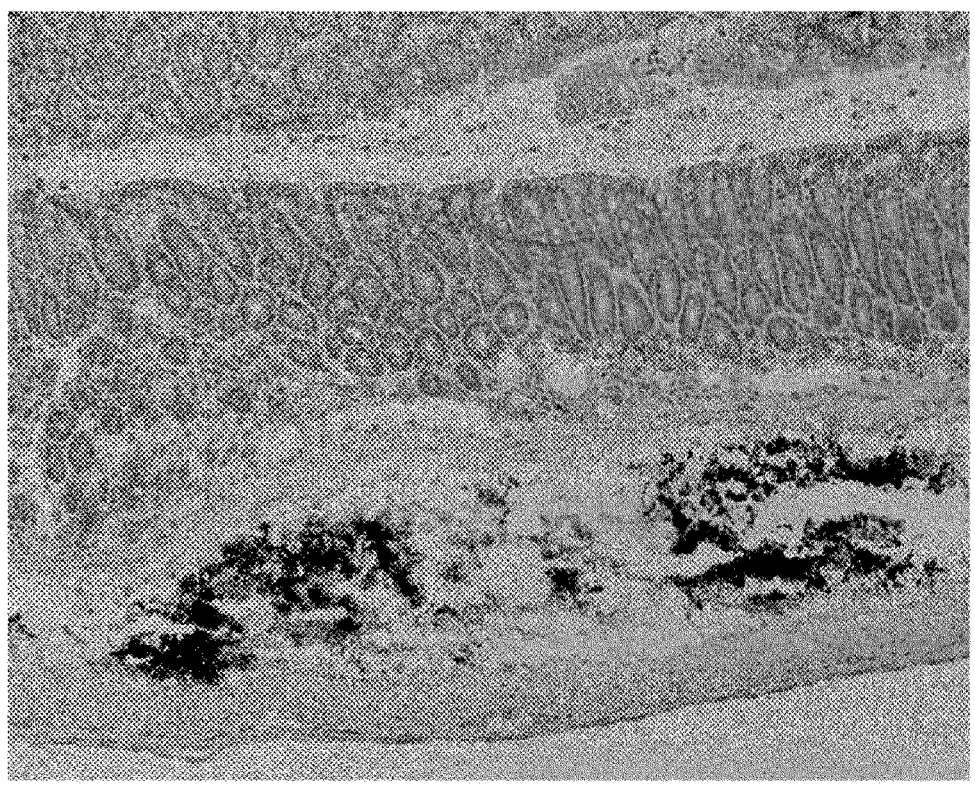

FIG. 3 is a photograph showing retention of a substance administered into the submucous tissue of the large intestine in a normal mouse. Carbon particles (black) were retained within the submucous tissue of the large intestine.

Figure 4:
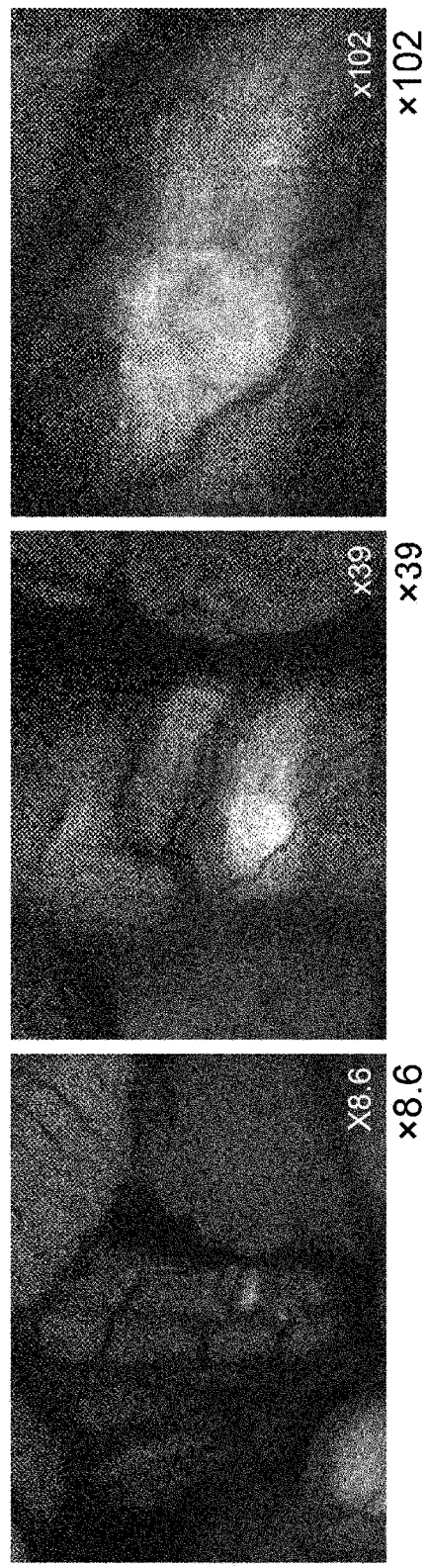

FIG. 4 show photographs depicting retention of a nucleic acid administered into the submucous tissue of the large intestine in a normal mouse. FITC-labeled siRNA (green) was retained at a specific site in the large intestine. Images obtained with a fluorescence stereoscopic microscope; the magnification is 8.6-, 39-, or 102-fold from left.

Figure 5:
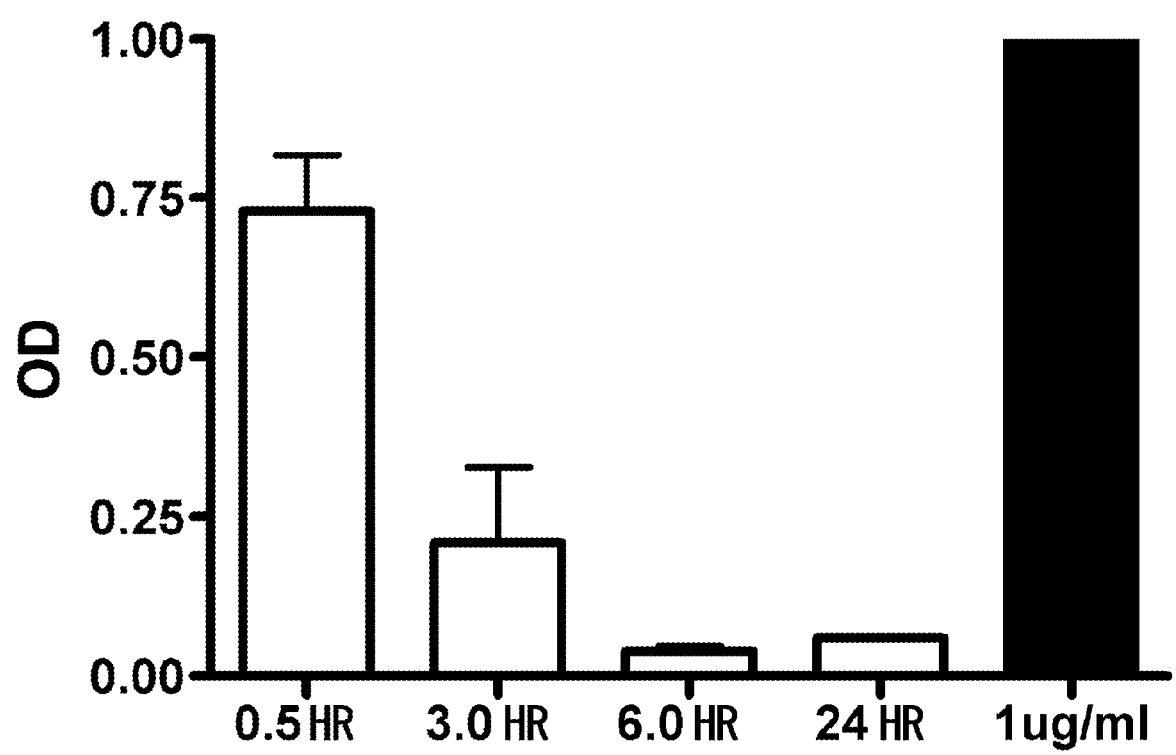

FIG. 5 is a graph showing the kinetics of a nucleic acid administered into the submucous tissue of the large intestine in a normal mouse. The graph shows the concentrations of siRNA retained in the large intestine 0.5, 3, 6, and 24 hours after injection into the submucous tissue of the large intestine. The rightmost bar (black) is a positive control, indicating the siRNA concentration before injection.

Figure 6:
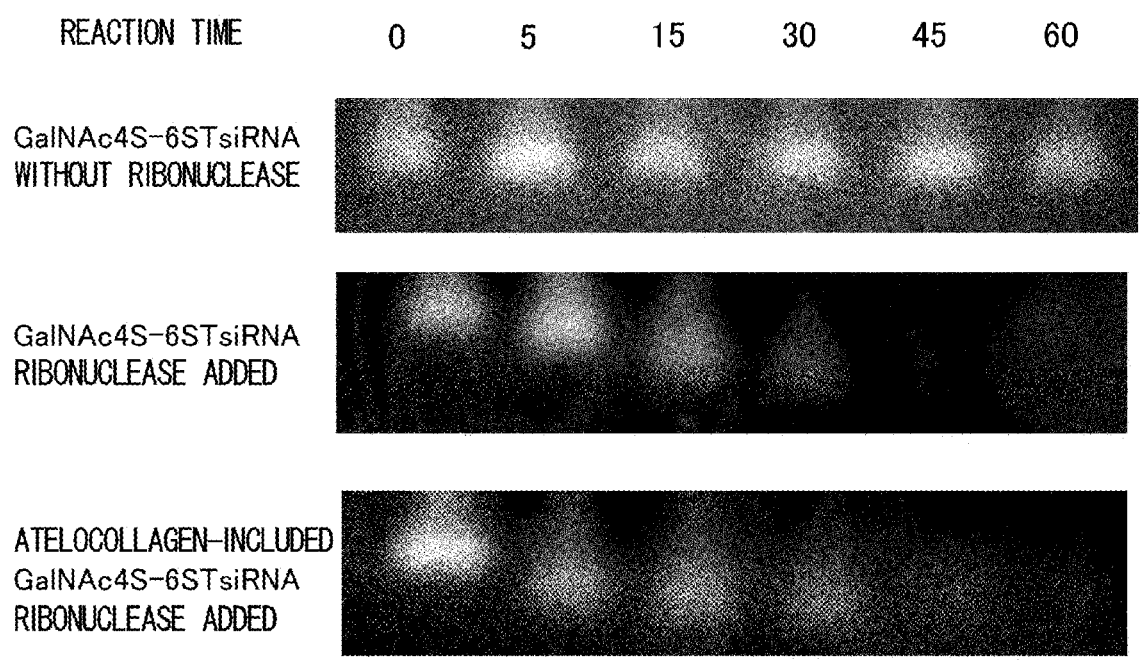

FIG. 6 shows a result of agarose gel electrophoresis after stability test at 37° C. The upper panel shows the pattern of GalNAc4S-6ST siRNA alone; the middle panel shows the pattern of GalNAc4S-6ST siRNA treated with ribonuclease; the bottom panel shows atelocollagen-embedded GalNAc4S-6ST siRNA treated with ribonuclease. The time shows the duration of reaction at 37° C.

Figure 7:
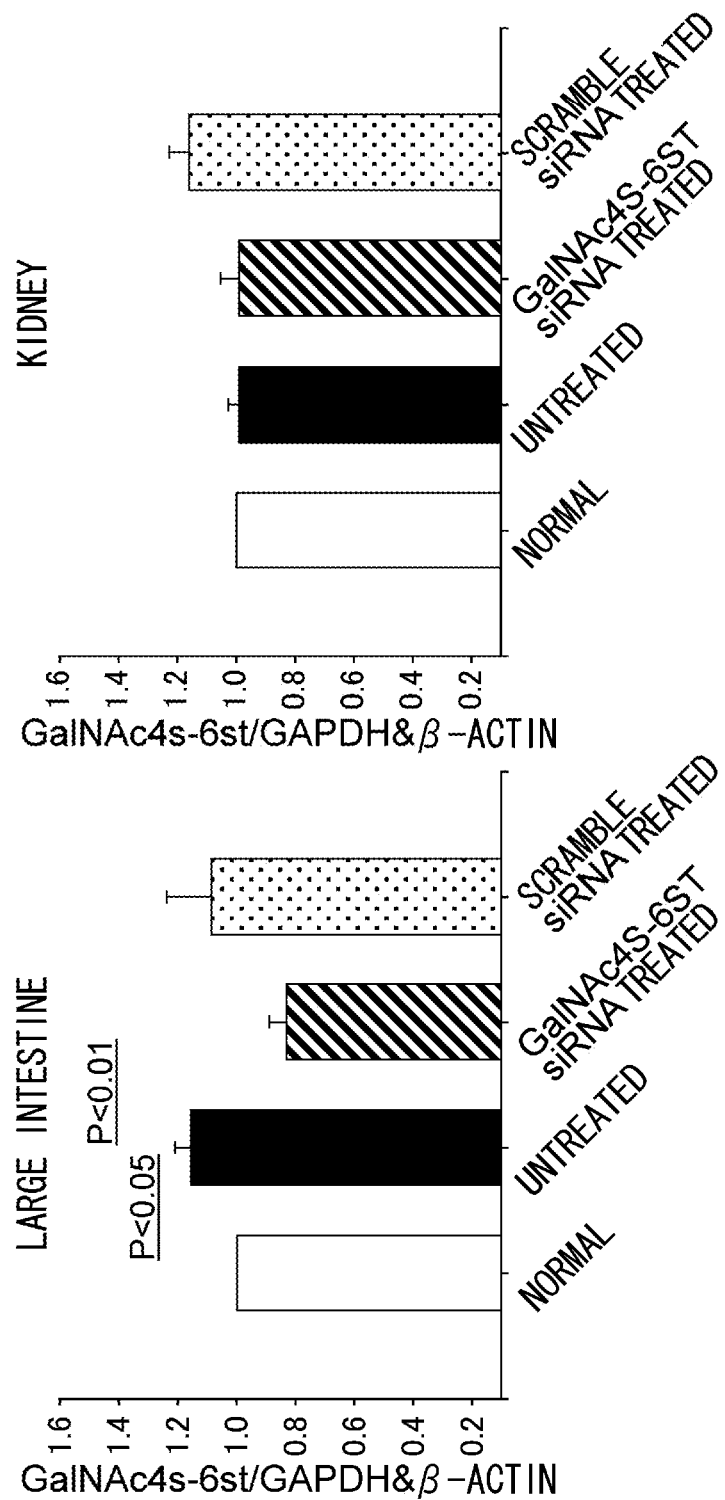

FIG. 7 show graphs depicting the results on the effect of a nucleic acid administered into the submucous tissue of the large intestine in dextran sulfate sodium (DSS)-induced colitis model mice. In the DSS colitis model, the siRNA injected into the submucous tissue of the large intestine suppressed the enhanced expression of GalNAc4S-6ST in the large intestine. Meanwhile, the siRNA had no effect in the kidney.

Figure 8:
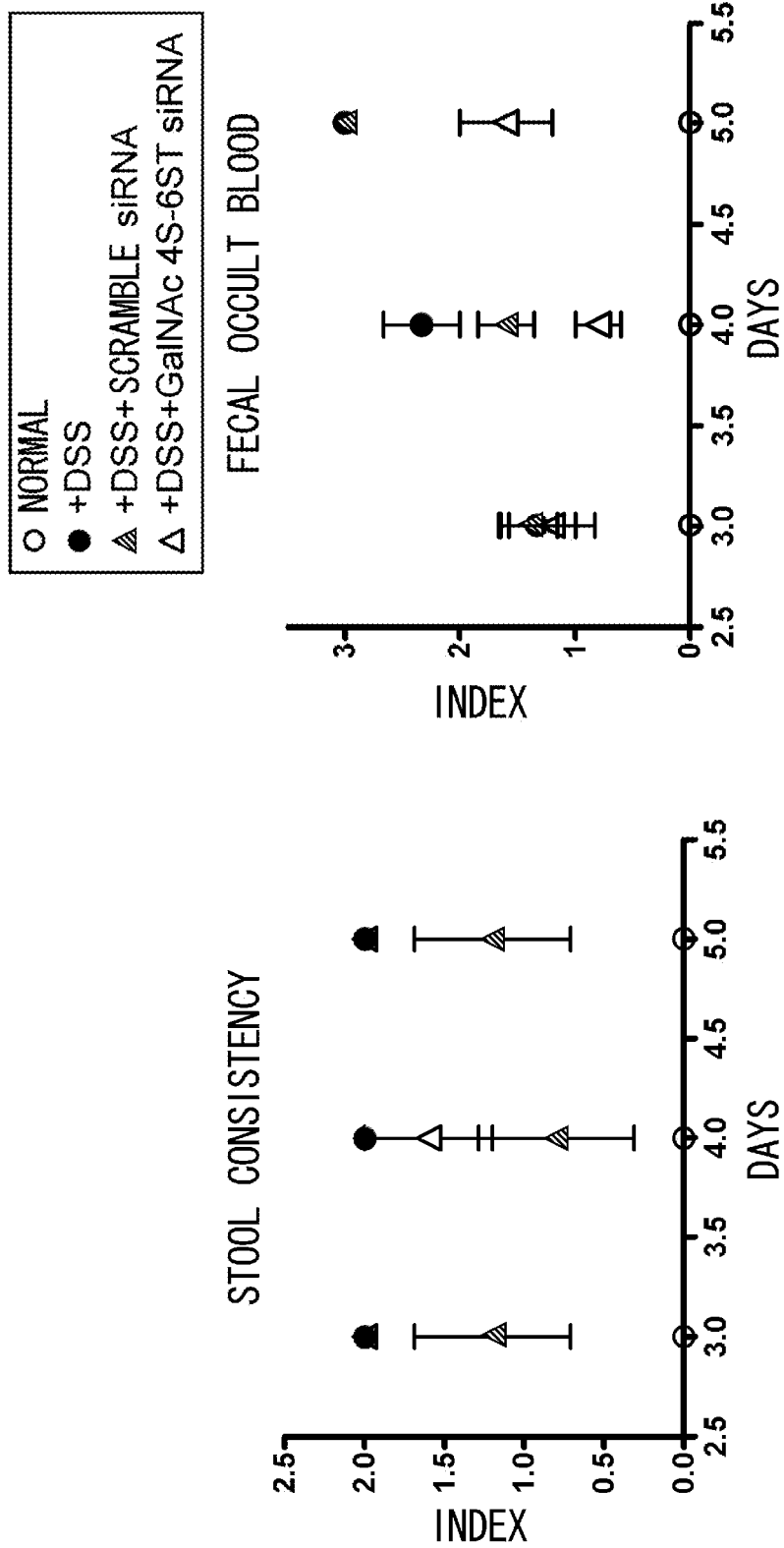

FIG. 8 show graphs depicting an inflammatory activity-suppressing effect of a nucleic acid administered into the submucous tissue of the large intestine in DSS colitis model mice. The left panel shows stool consistency, while the right panel shows fecal occult blood. The administration of siRNA into the submucous tissue of the large intestine resulted in suppression of disease activity.

Figure 9:
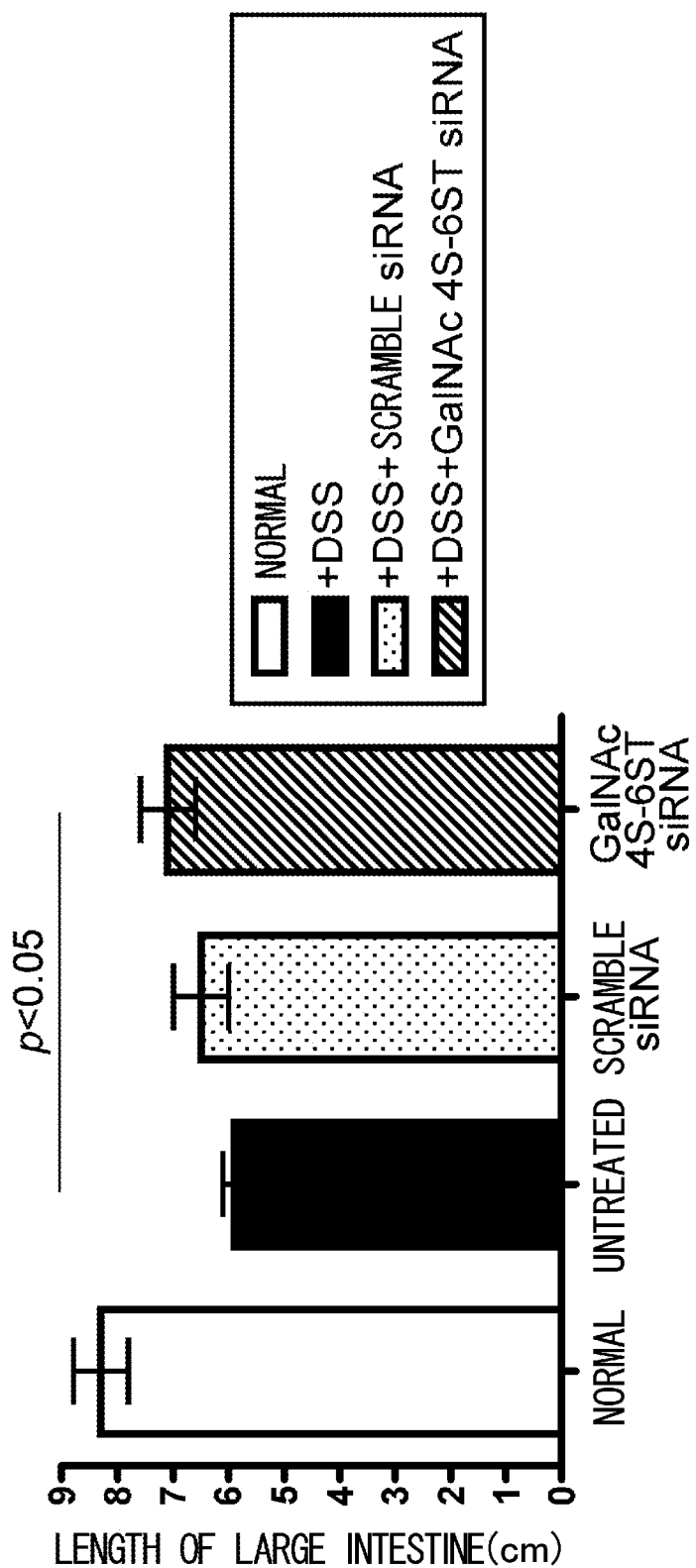

FIG. 9 is a graph showing the colonic length-improving effect of a nucleic acid administered into the submucous tissue of the large intestine in DSS colitis model mice. The administration of siRNA into the submucous tissue of the large intestine significantly suppressed the contraction of large intestine.

Figure 10:
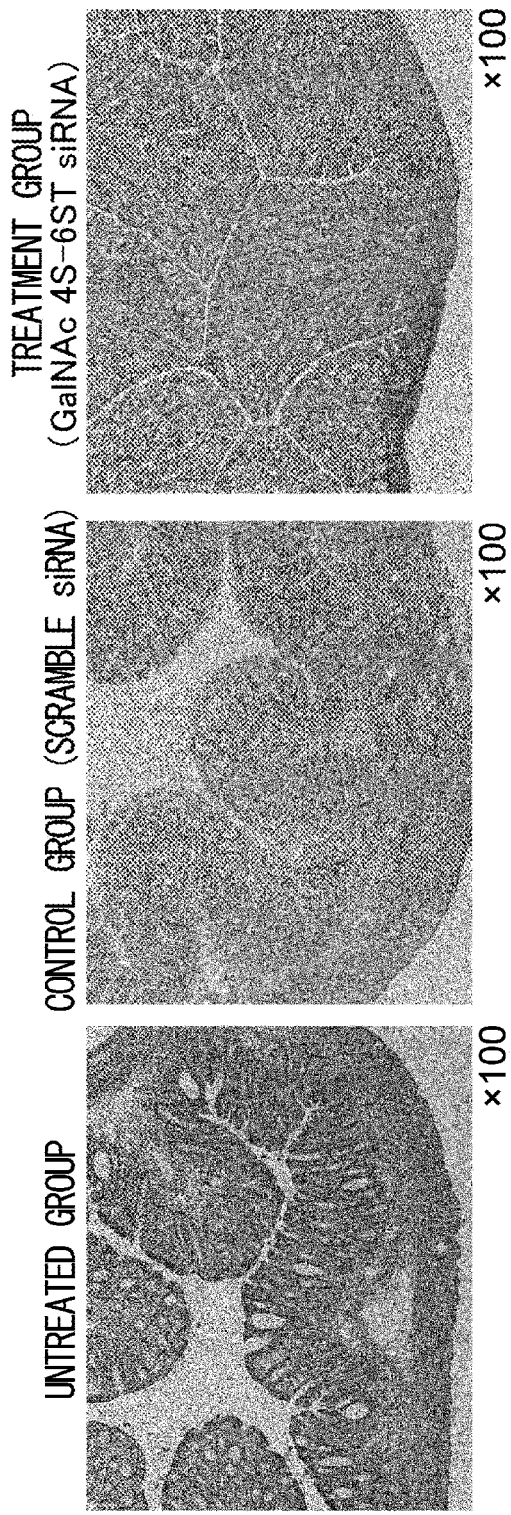

FIG. 10 show photographs depicting the tissue-improving effect of a nucleic acid administered into the submucous tissue of the large intestine in DSS colitis model mice. The administration of siRNA into the submucous tissue of large intestine significantly suppressed the epithelial disruption, inflammation, and fibrosis associated with colitis. HE stain; 100-fold magnification.

BEST MODE FOR CARRYING OUT THE INVENTION

The present inventors discovered that by directly administering physiologically active substances into submucous tissues, these physiologically active substances are retained at the administration sites over a long period without loss or diffusion, and exert effects acting as a reservoir.

The present invention provides methods for retaining and expressing physiologically active substances in a target tissue-specific manner, in which the physiologically active substances are administered to the submucous tissue.

Herein, "mucous" ("mucosa") more specifically refers to the macroscopic membrane covering the surface of the lumen of hollow organs such as the gastrointestinal tract, respiratory and urogenital systems, including membranes covering the surface of auditory tubes, the middle ear cavity connecting to the airway, and bulbar and palpebral conjunctivae. Normally, epithelium is the outermost layer, and the underlayer is lamina propria of the mucous membrane.

As used herein, "submucous tissue (tela submucosa)" refers to the tissue under the lamina propria that supports the epithelium. In actual clinical practice, however, a "submucous tissue" may be distinguished depending on a physician's "feeling", and thus the subepithelial tissue may be taken as "intramucosal tissue" and deeper tissue between the mucosa and muscle may be identified as "submucous tissue".

In the present invention, the "submucous tissue" is not particularly limited, as long as its properties (pH, sugar chains, cellular composition, etc.) are appropriate to maintain the physiologically active substances of the present invention. Such submucous tissues include, for example, those of the intestinal tract, eye, ear, nose, uterus, urinary bladder, or oral cavity, subcutaneous tissues, or such, but are not limited to these examples.

In particular, the submucous tissues of the intestinal tract have been demonstrated to be much more effective than other matrices when pancreatic Langerhans islets are cultured in vitro (Tian X H et al. Hepatobiliary Pancreat Dis Int. 4: 524, 2005). This also suggests that the submucous tissues of the intestinal tract may have a very special microenvironment. More specifically, in a preferred embodiment of the present invention, submucous tissues include those of the intestinal tract.

Such "submucous tissues of the intestinal tract" include, for example, those of intestinal tracts such as the esophagus, stomach, duodenum, small intestine, appendix, large intestine, and rectum. In a preferred embodiment of the present invention, submucous tissues of the intestinal tract include submucous tissue of the large intestine.

Herein, "physiologically active substance" is a general name for chemical substances that exert various biological effects in living organisms, and is not particularly limited. In the present invention, a physiologically active substance is preferably selected, for example, from nucleic acids, proteins, carbohydrates, lipids, or low-molecular-weight compounds.

"Nucleic acids" used in the present invention refer to both RNAs and DNAs. Chemically synthesized nucleic acid analogs, such as so-called "PNAs" (peptide nucleic acids) or Morpholino antisense oligos, are also included in the nucleic acids of the present invention. PNAs are nucleic acids in which the fundamental backbone structure of nucleic acids, the pentose-phosphate backbone, is replaced by a polyamide backbone with glycine units, and Morpholino antisense oligos are nucleic acids in which the pentose-phosphate backbone is replaced by a morpholino backbone. PNAs and morpholino antisense oligos have a three-dimensional structure quite similar to that of nucleic acids.

For suppressing the expression of objective (target) genes, nucleic acids of the present invention include, for example, antisense nucleic acids against transcripts of target genes or portions thereof, nucleic acids with the ribozyme activity of specifically cleaving transcripts of target genes, and nucleic acids with the activity of using RNAi effect to inhibit the expression of target genes.

Methods for suppressing the expression of specific endogenous genes using antisense technology are well known to those skilled in the art. There are a number of causes for the action of antisense nucleic acids in suppressing target gene expression, including:

inhibition of transcription initiation by triplex formation;

transcription inhibition by hybrid formation at a site with a local open loop structure generated by an RNA polymerase;

transcription inhibition by hybrid formation with the RNA being synthesized;

splicing inhibition by hybrid formation at an intron-exon junction;

splicing inhibition by hybrid formation at the site of spliceosome formation;

inhibition of transport from the nucleus to the cytoplasm by hybrid formation with mRNA;

translation initiation inhibition by hybrid formation at the capping site or poly(A) addition site;

inhibition of translation initiation by hybrid formation at the translation initiation factor binding site;

inhibition of translation by hybrid formation at the ribosome binding site adjacent to the initiation codon;

inhibition of peptide chain elongation by hybrid formation in the translational region of mRNA or at the polysome binding site of mRNA; and inhibition of gene expression by hybrid formation at the protein-nucleic acid interaction sites (Hirashima and Inoue, Shin Seikagaku Jikken Koza 2 (New Courses in Experimental Biochemistry 2), Kakusan (Nucleic Acids) IV: "Idenshi no Fukusei to Hatsugen (Gene replication and expression)", Ed. The Japanese Biochemical Society, Tokyo Kagakudojin, 1993, pp. 319-347). There are causes for the action of antisense RNA in suppressing target gene expression includes inhibition of gene expression by RNAi effect of double-stranded RNA formation by hybrid formation with mRNA, and such. Thus, antisense nucleic acids inhibit the expression of target genes by inhibiting various processes, such as transcription, splicing, and translation.

The antisense nucleic acids may inhibit the expression and/or function of target genes, based on any of the actions described above. In one embodiment, antisense sequences designed to be complementary to an untranslated region adjacent to the 5' end of an mRNA for a target gene may be effective for inhibiting translation of the gene. Sequences complementary to a coding region or 3'-untranslated region can also be used. Thus, the antisense nucleic acids to be used in the present invention include not only nucleic acids comprising sequences antisense to the coding regions, but also nucleic acids comprising sequences antisense to untranslated regions of target genes. Such antisense nucleic acids to be used are linked downstream of adequate promoters and are preferably linked with transcription termination signals on the 3' side. Nucleic acids thus prepared can be introduced into desired animals (cells) using known methods. The sequences of the antisense nucleic acids are preferably complementary to a target gene or portion thereof that is endogenous to the animals (cells) to be transformed with them. However, the sequences need not be perfectly complementary, as long as the antisense nucleic acids can effectively suppress expression of a gene. The transcribed RNAs preferably have 90% or higher, and most preferably 95% or higher complementarity to target gene. To effectively inhibit target gene expression using antisense nucleic acids, the antisense nucleic acids are preferably at least 15 nucleotides long, and less than 25 nucleotides long. However, the lengths of the antisense nucleic acids of the present invention are not necessarily limited to the lengths mentioned above, and they may be 100 nucleotides or more, or 500 nucleotides or more.

Expression of the above-mentioned target genes can also be inhibited using ribozymes or ribozyme-encoding DNAs. Ribozymes refer to RNA molecules with catalytic activity. There are various ribozymes with different activities. Among others, studies that focused on ribozymes functioning as RNA-cleaving enzymes have enabled the design of ribozymes that cleave RNAs in a site-specific manner Some ribozymes have 400 or more nucleotides, such as group I intron type ribozymes and M1 RNA, which is comprised by RNase P, but others, called hammerhead and hairpin ribozymes, have a catalytic domain of about 40 nucleotides (Koizumi, M. and Otsuka, E., Tanpakushitsu Kakusan Koso (Protein, Nucleic Acid, and Enzyme) 1990, 35, 2191).

For example, the autocatalytic domain of a hammerhead ribozyme cleaves the sequence G13U14C15 at the 3' side of C15. Base pairing between U14 and A9 has been shown to be essential for this activity, and the sequence can be cleaved when C15 is substituted with A15 or U15 (Koizumi, M. et al., FEBS Lett. 1988, 239, 285; Koizumi, M. and Otsuka, E., Tanpakushitsu Kakusan Koso (Protein, Nucleic Acid, and Enzyme) 1990, 35, 2191; and Koizumi, M. et al., Nucl. Acids Res. 1989, 17, 7059).

In addition, hairpin ribozymes are also useful. Such ribozymes are found in, for example, the minus strand of satellite RNAs of tobacco ringspot viruses (Buzayan, J. M., Nature 1986, 323, 349). It has been shown that target-specific RNA-cleaving ribozymes can also be created from hairpin ribozymes (Kikuchi, Y. and Sasaki, N., Nucl Acids Res. 1991, 19, 6751; and Kikuchi, Y. Kagaku to Seibutsu (Chemistry and Biology) 1992, 30, 112). Thus, the expression of the above-described target genes can be inhibited by using ribozymes to specifically cleave the gene transcripts.

Furthermore, in a preferred embodiment, nucleic acids of the present invention include nucleic acids with the inhibition activity of using RNAi effect (siRNA).

The expression of target genes can be suppressed by RNA interference (hereinafter abbreviated as "RNAi"), using double-stranded RNAs comprising a sequence the same as or similar to a target gene sequence.

RNAi is a phenomenon where an mRNA comprising a base sequence complementary to a double-stranded RNA is degraded. RNAi is a method based on this phenomenon, in which the expression of an arbitrary gene is suppressed by artificially introducing a 21- to 23-mer double-stranded RNA (small interfering RNA; siRNA). In 1998, Fire et al. discovered using *C. elegans* that double-stranded RNA silences genes in a sequence-specific manner (Fire, A. et al., Nature 1998, 391, 806-811). After elucidating the underlying mechanism of mRNA cleavage by 21- to 23-mer processed double-stranded RNA (Zamore P D. et al., Cell 2000, 101, 25-33), identifying RNA-induced silencing complex (RISC) (Hammond, S. M. et al., Science 2001, 293, 1146-1150), and cloning Dicer (Bernstein, E. et al., Nature, 409, 363-366), Elbashir et al. demonstrated in 2001 that siRNA could also suppress expression in a sequence-specific manner in mammalian cells (Elbashir S M. et al., Nature 2001, 411, 494-498). Thus, application of RNAi to gene therapy is expected.

Nucleic acids with inhibitory activity based on RNAi effect are generally referred to as siRNAs or short hairpin RNAs (shRNAs). RNAi is a phenomenon in which, when cells or such are introduced with short double-stranded RNAs (hereinafter abbreviated as "dsRNAs") comprising sense RNAs that comprise sequences homologous to the mRNAs of a target gene, and antisense RNAs that comprise sequences homologous to a sequence complementary thereto, the dsRNAs bind specifically and selectively to the target gene mRNAs, induce their disruption, and cleave the gene transcript, thereby effectively inhibiting (suppressing) target gene expression. For example, when dsRNAs are introduced into cells, the expression of genes with sequences homologous to the RNAs is suppressed (the genes are knocked down). As described above, RNAi can suppress the expression of target genes, and is thus drawing attention as a method applicable to gene therapy, or as a simple gene knockout method replacing conventional methods of gene disruption, which are based on complicated and inefficient homologous recombination. The RNAs to be used in RNAi are not necessarily perfectly identical to the target genes or portions thereof; however, the RNAs are preferably perfectly homologous to the genes or portions thereof.

The targets of the siRNAs to be designed are not particularly limited, as long as they are regions of target genes. Any region of the gene can be a candidate for a target.

The double-stranded RNA described above may also be closed at one end with a hairpin structure (shRNAs). shRNAs are RNA molecules with a stem-loop structure, since a portion of the single strand constitutes a strand complementary to another portion. Thus, molecules capable of forming an intramolecular double-stranded RNA are also included in the siRNAs.

For example, even double-stranded RNAs with a structure having a deletion or addition of one or a small number of bases are included in the siRNAs of the present invention, as long as they have the function of suppressing the expression of target genes by RNAi effect.

Some details of the RNAi mechanism still remain poorly understood, but it is known that an enzyme called "DICER" (a member of the RNase III nuclease family) binds to a double-stranded RNA and degrades it in to small fragments, called "siRNAs". The double-stranded RNAs of the present invention that have RNAi effect include such double-stranded RNAs prior to being degraded by DICER. Specifically, since even long RNAs that have no RNAi effect when intact can be degraded into siRNAs which have RNAi effect in cells, the length of the double-stranded RNAs of the present invention is not particularly limited.

For example, long double-stranded RNAs covering the full-length or near full-length mRNA of a target gene can be pre-digested, for example, by DICER, and then the degradation products can also be used. These degradation products are expected to contain double-stranded RNA molecules with RNAi effect. With this method, it is not necessary to specifically select the regions expected to have RNAi effect. In other words, it is not necessary to accurately determine regions with RNAi effect in the mRNAs of the genes described above.

The siRNAs of the present invention are not necessarily single pairs of double-stranded RNAs directed to target sequences, but may be mixtures of multiple double-stranded RNAs directed to regions that cover the target sequence. The siRNAs of the present invention include so-called "siRNA cocktails".

All nucleotides in the siRNAs of the present invention do not necessarily need to be ribonucleotides (RNAs). Specifically, one or more of the ribonucleotides constituting the siRNAs of the present invention may be replaced with corresponding deoxyribonucleotides. The term "corresponding" means that although the sugar moieties are structurally differently, the nucleotide residues (adenine, thymine (uracil), guanine, or cytosine) are the same. For example, deoxyribonucleotides corresponding to ribonucleotides with adenine refer to deoxyribonucleotides with adenine. The term "or more" described above is not particularly limited, but preferably refers to a small number of about two to five ribonucleotides.

The siRNAs of the present invention include, for example, the siRNAs of SEQ ID NOs: 1 and/or 2.

In another embodiment, nucleic acids aiming at suppressing the expression of a target gene includes microRNAs (miRNAs), aptamers, and locked nucleic acids (LNAs) generated by modifying oligonucleotides.

In the present invention, such nucleic acids are not limited to the examples described above, and it is possible to use nucleic acids that are appropriate for the purposes.

In addition, the "protein" of the present invention refers to a polymer comprising several amino acids, and includes not only polypeptides but also oligopeptides. Herein, polypeptides include both naturally-occurring polypeptides without modification and modified polypeptides. Such modifications include acetylation, acylation, ADP-ribosylation, amidation, covalent bonding of flavin, covalent bonding of heme moiety/moieties, covalent bonding of nucleotides or nucleotide derivatives, covalent bonding of lipids or lipid derivatives, covalent bonding of phosphatidylinositol, cross-linking, cyclization, disulfide bond formation, demethylation, formation of covalent cross-links, formation of cystine, formation of pyroglutamate, formylation, γ-carboxylation, glycosylation, formation of GPI anchors, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

For inhibiting (suppressing) the function of a (target) protein, proteins of the present invention include, for example, a target protein variants, which are dominant negative for the target protein, and antibodies that bind to the target protein.

"A target protein variant that is dominant negative for a target protein" refers to a protein that, when expressed a gene encoding the protein, has the function of reducing or eliminating the activity of the endogenous wild type protein.

Moreover, antibodies that bind to the target protein can be prepared by methods known to those skilled in the art. Polyclonal antibodies can be obtained, for example, by the following procedure: small animals such as rabbits are immunized with a natural target protein or a recombinant target protein expressed in microorganisms such as E. coli as a fusion protein with GST, or a partial peptide thereof. Sera are obtained from these animals and purified by, for example, ammonium sulfate precipitation, Protein A or G columns, DEAE ion exchange chromatography, affinity columns coupled with the target protein or a synthetic peptide to prepare antibodies. Monoclonal antibodies can be obtained, for example, by the following procedure: small animals such as mice are immunized with a target protein or a partial peptide thereof. Spleens are removed from the mice and crushed to isolate cells. The cells are fused with mouse myeloma cells using a reagent such as polyethylene glycol. Clones producing antibodies that bind to a target protein is selected from among the resulting fused cells (hybridomas). The obtained hybridomas are then transplanted in the peritoneal cavities of mice, and ascites collected. The obtained monoclonal antibodies can be purified by, for example, ammonium sulfate precipitation, Protein A or G columns, DEAE ion exchange chromatography, affinity columns coupled with the target protein or a synthetic peptide.

The forms of above-described antibodies are not particularly limited as long as they bind to a target protein. The antibodies of the present invention may include human antibodies, humanized antibodies created by gene recombination, fragments or modified products of such antibodies, in addition to the polyclonal and monoclonal antibodies described above.

The target proteins used as sensitizing antigens to prepare antibodies are not limited in terms of the animal species from which the proteins are derived. However, the proteins are preferably derived from mammals, for example, mice and humans Human-derived proteins are particularly preferred. The proteins to be used as sensitizing antigens may be whole proteins or partial peptides thereof. Such partial peptides of the proteins include, for example, amino (N)-terminal fragments and carboxyl (C)-terminal fragments of the proteins. Herein, "antibodies" refer to antibodies that react with a full-length protein or fragment thereof.

In addition to immunizing nonhuman animals with antigens to obtain the above hybridomas, human lymphocytes, for example, EB virus-infected human lymphocytes, can be sensitized in vitro with the proteins or with cells expressing the proteins, or with lysates thereof, and the sensitized lymphocytes can be fused with human-derived myeloma cells with the ability to divide permanently, for example, U266, to obtain hybridomas that produce desired human antibodies with binding activity to the proteins.

When using the prepared antibodies for human administration (antibody therapy), the antibodies are preferably human or humanized antibodies in order to reduce immunogenicity.

In another embodiment of the present invention, proteins include, for example, enzymes; and their forms are not particularly limited.

Herein, "carbohydrates" include all of monosaccharides, oligosaccharides, and polysaccharides. The carbohydrates of the present invention also include complex carbohydrates in which the above saccharides are covalently linked to proteins or lipids, and glycosides in which the reducing groups of monosaccharides or oligosaccharides are linked to an aglycon such as alcohol, phenol, saponin, or a pigment.

Herein, "lipids" include all of simple lipids, complex lipids, and derived lipids.

Herein, "low-molecular-weight compounds" include chemically synthesized substances with a low molecular weight, typically ranging from about several hundreds to thousands. For inhibiting (suppressing) the function of a target protein, it is possible to use, for example, low-molecular-weight substances that bind to the target protein. Such low-molecular-weight substances that bind to a target protein may be natural or artificial compounds. In general, the compounds can be obtained or produced by methods known to those skilled in the art.

In another embodiment of the present invention, the physiologically active substances are not limited, and include, for example, single compounds such as natural compounds, organic compounds, inorganic compounds; and compound libraries, expression products of gene libraries, cell extracts, cell culture supernatant, products of fermenting microorganisms, extracts of marine organisms, and plant extracts. Each of the above-described physiologically active substances may be used alone or in combination with other physiologically active substances.

In the present invention, the physiologically active substances are preferably used (administered) in an unmodified, non-labeled form (occasionally herein referred to as "naked form").

The physiologically active substances of the present invention can be used after labeling, if needed. Such labels include, for example, radioisotope labels and fluorescent labels. The labels are not particularly limited, and include alkaline phosphatase labels, peroxidase labels, biotin-labeled/streptavidin-conjugated enzymes (alkaline phosphatase, peroxidase, and such), and fluorescein isothiocyanate (FITC).

Furthermore, the physiologically active substances of the present invention can be used in combination with pharmaceutically acceptable carriers. Herein, the "pharmaceutically acceptable carriers" include, for example, vectors that are typically used as gene therapy vectors.

The above-described vectors include, for example, viral vectors such as retroviral vectors, adenoviral vectors, and adeno-associated viral vectors, and non-viral vectors such as liposomes and atelocollagen. Using the vectors, the physiologically active substances of the present invention can be administered by ex vivo and in vivo methods.

Other than the carriers described above, the carriers of the present invention include, but are not limited to, for example, water, physiological saline, phosphate buffered saline, polyvinyl alcohol, polyvinylpyrrolidone, carboxylvinyl polymer, sodium alginate, water-soluble dextran, pectin, xanthan gum, gum Arabic, gelatin, agar, glycerin, propylene glycol, polyethylene glycol, vaseline, paraffin, stearyl alcohol, stearic acid, human serum albumin, mannitol, sorbitol, and lactose. The physiologically active substances of the present invention may further comprise additives such as preservatives. The physiologically active substances of the present invention may further comprise other pharmacological ingredients.

The physiologically active substances of the present invention are preferably parenteral preparations; liquid preparations such as solutions and suspensions are preferred, including, for example, injections. Other preferred dosage forms include, for example, liniments and coating agents which are applied onto or coat the surface of indwelling devices such as balloons and stents.

The physiologically active substances of the present invention can be administered to subjects (patients or such) by methods known to those skilled in the art, such as using injection into target submucous tissues, or application or coating onto the surface of indwelling devices such as balloons and stents. If needed, devices such as endoscopes may be used to administer the physiologically active substances.

The applied dose of a physiologically active substance of the present invention varies depending on the body weight and age of the subject (patient or such), administration method, and the like; however, the optimum dose can be appropriately selected by those skilled in the art.

The present invention also provides methods for treating or preventing diseases, which comprise the step of retaining and expressing the physiologically active substances in a target tissue-specific manner affected with the diseases, by administering the physiologically active substances to the submucous tissues with diseases.

The above-described "diseases" include those associated with mucosa (specifically, inflammatory bowel disease and Crohn's disease), fibrotic diseases, arthritis (osteoarthritis and rheumatoid arthritis), Alzheimer's disease, organ transplant toxicity and rejection, cachexia, allergy, cancer (for example, solid tumors/cancers including colon, breast, prostate, and brain, and malignant hematopoietic tumors including leukemia and lymphoma), tissue ulceration, restenosis, periodontal diseases, bullous epidermolysis, osteoporosis, loosening of artificial joint implants, atherosclerosis (including divulsion of atherosclerosis leison), aortic aneurysm (including abdominal aneurysm and cerebral aneurysm), congestive heart failure, myocardial infarct, seizure, cerebral ischemia, head injury, spinal cord injury, neurodegenerative disorders (acute and chronic), autoimmune diseases, Huntington's chorea, Parkinson's disease, migraine, depression, peripheral neuropathy, pain, cerebral amyloid angiopathy, nootropic or cognitive enhancement, amyotrophic lateral sclerosis, multiple sclerosis, ophthalmovascular formation, conical injury, macular degeneration, abnormal healing of traumatic injury, and burns; however, the diseases are not limited to the above examples, and include other diseases as long as the methods of the present invention are applicable to them.

Preferred subjects to be administered with the physiologically active substances of the present invention are mammals including humans, and domestic animals, pets, and experimental animals. In particular, mammals (patients) with a disease described above are preferred subjects in the present invention.

All publications, patents, and patent applications cited herein are incorporated herein by reference in their entirety.

EXAMPLES

Hereinbelow, the present invention is specifically described using Examples; however, it is not to be construed as being limited thereto.

Example 1

DSS enteritis was induced by allowing 12-week-old male Wistar rats to freely drink water containing 3% dextran sulfate sodium (DSS) (molecular weight; 50,000) (Okayasu I, Hatakeyama S, Ohkusa T, Inagaki Y, Nakaya R. A novel method in the induction of reliable experimental acute and chronic ulcerative colitis in mice. Gastroenterology 1990, 98: 694-702). An ultrathin endoscope for humans was inserted into the large intestines of rats anesthetized with Nembutal on day 0 and 3 after the start of feeding with DSS water. After observation of the mucosa, siRNA was injected into the submucous tissue at equally spaced four sites in the left colon. The ultrathin endoscope used was a prototype model (outer diameter of the scope, 5.6 mm) having a working forceps channel (channel diameter, 2 mm) which had been developed as an upper gastrointestinal endoscope for humans by OLYMPUS. Untreated rats were used as a control.

The therapeutic effect was evaluated based on: (1) clinical disease activity index (CDAI) determined in terms of the three items: weight loss, diarrhea, and melena; (2) intestinal length; and (3) pathohistological analysis of HE stained samples prepared using section of large intestine, in the treated and control groups.

Example 2

Retention of Physiologically Active Substances in the Submucous Tissue of Rat Large Intestine Next, the retention of physiologically active substances in the submucous tissue of normal rats was analyzed by diagnostic imaging using X-ray and CT, which are routinely used clinically. Twelve-week-old male Wistar rats were anesthetized with Nembutal, and then an ultrathin endoscope for humans was inserted into the large intestines and 20 µl of iopamidol, a contrast medium, was endoscopically injected alone into the submucous tissue of the left colon using a local injection needle.

Iopamidol refers to the compound named N,N'-Bis[2-hydroxy-1-(hydroxymethyl)ethyl]-5-[(2S)-2-hydroxypropanoylamino]-2,4,6-triiodoisophthalamide ($C_{17}H_{22}I_3N_3O_8$; molecular weight, 777.09) represented by formula (I):

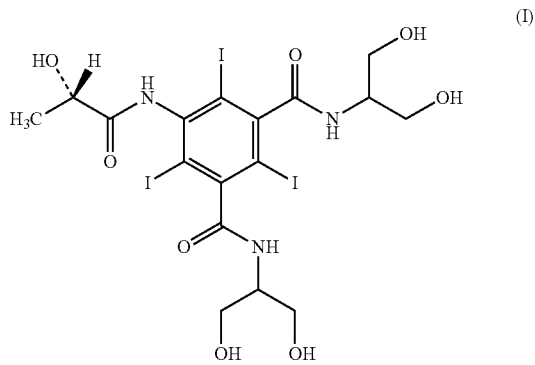 [SMILES: C[C@H](O)C(=O)Nc1c(I)c(C(=O)NC(CO)CO)c(I)c(C(=O)NC(CO)CO)c1I]

X-ray photography and CT scanning was carried out after one hour. The results are shown in FIG. 2. The X-ray images showed that the injected iopamidol was retained in the submucous tissue of the colon without intraperitoneal leakage and transfer to other sections. The CT images also showed that the injected iopamidol was retained specifically at the injection sites and did not spread to other slices. Thus, the clinical evaluation method also demonstrated that the methods of the present invention could retain physiologically active substances very specifically within target submucous tissues.

Example 3

Retention of Physiologically Active Substances in the Submucous Tissue of Mouse Large Intestine Next, the retention of physiologically active substances was assessed using mice, which are more common experimental animals. Eight-week-old female C57BL/6J mice were anesthetized with Nembutal and laparotomized to expose the lower part of the large intestines. 20 µl of carbon particles (India ink), corresponding to a physiologically active substance of the present invention, alone was macroscopically injected to the submucous tissues. Then, the abdomen was closed.

Five days after, the mice were sacrificed to prepare tissue sections of the large intestine. The sections were observed under a light microscope. The result is shown in FIG. 3. The injected carbon particles were found to be retained within the submucous tissue without physical diffusion and leakage to other portions.

Example 4

Local Retention of Nucleic Acid within Mouse the Large Intestine

20 µl of FITC-labeled siRNA (20 µM) of BLOCK-iT Fluorescent Oligo (Invitrogen) was injected into the submucous tissue of mouse large intestine by the same method as described in Examples 1 and 3. The retention of the injected siRNA was assessed under a fluorescent stereomicroscope (Leica) 24 hours after injection.

Figure 1:
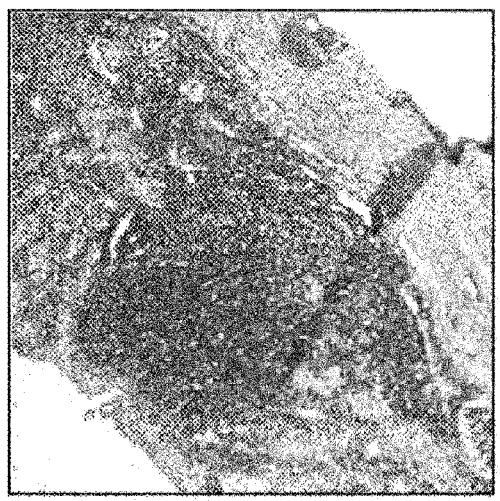
FIG. 1 show photographs of histological images 24 hours after injection of FITC-labeled siRNA into the submucous tissues of rat large intestines. The images show retention of the siRNA in the submucous tissues.
Figure 1:
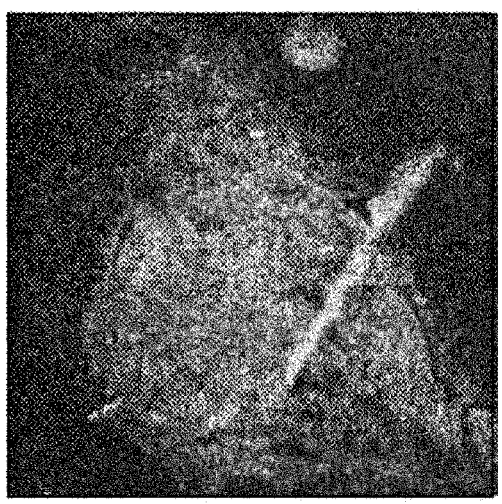
Figure 1:

The results are shown in FIG. 4. The FITC-labeled siRNA was confined at the injection site in the large intestine. FIG. 1 of Example 1 is a histological image obtained by injecting the same FITC-labeled siRNA into the submucous tissue of rat large intestine. Based on the findings described above, the same result is predicted to be obtained when the labeled siRNA is injected into the submucous tissue of mouse large intestine.

From the result described above, from all different points of view using clinical index (X-ray and CT), microscopic indicators in living subjects, and histological index, it was demonstrated that, when injected into the submucous tissue of large intestine by the method of the present invention, physiologically active substances, including siRNA, were selectively retained within the submucous tissue.

Example 5

Nucleic Acid Kinetics in the Submucous Tissue of Mouse Large Intestine

Next, in order to also confirm the retention of injected siRNA in the submucous tissue of the large intestine by biochemical methods, the concentration of siRNA in the large intestine was determined by using the ELISA method for direct quantitation of siRNA according to a published report (Rosie Z et al. Analytical Biochem. 304: 19-25, 2002). The nucleotide sequences of GalNac 4S-6ST siRNA used in this Example are shown below, but the sequences are not limited to the example shown herein.

[human GalNac4-6ST siRNA] (Gene Bank accession number NM_015892)

(Hokkaido System Science Co., Ltd.)

```
                                              (SEQ ID NO: 1)
             5'-ggagcagagcaagaugaauacaauc-ag-3'

(SEQ ID NO: 2)
             3'-ua-ccucgucucguucuacuuauguuag-5'
```

GalNAc4S-6ST siRNA (0.3 µg/10 µl) was injected at three sites to the submucous tissue of large intestine in eight-week-old female C57BL/6J mice by the same method described in Example 3. The mice were sacrificed 0.5, 3, 6, or 24 hours after injection to prepare histological samples of the large intestine. The siRNA concentrations were determined by the ELISA methods.

The result is shown in FIG. 5. 1 µg/ml siRNA before injection was used as a positive control without any additional treatment. At the time point after 0.5 hour, the siRNA was retained at a very high concentration, while the concentration was decreased by half after three hours. However, the result shows that siRNA continually remained retained 24 hours later.

Thus, not only by diagnostic imaging and histology but also biochemically, it was proven that the physiologically active substances are effectively retained at the injection sites by the methods of the present invention.

Example 6

Stability Test for GalNAc4S-6ST siRNA

In this Example, GalNAc4S-6ST siRNA, the same substance used in Example 5, was assessed for its stability. First, test solutions were prepared by adding 1 µg of GalNAc4S-6ST siRNA to 200 µl of sterile phosphate buffer or 0.1% atelocollagen and stirring the mixtures at 4° C. for 20 minutes. 0.1% atelocollagen was prepared by combining 1% atelocollagen (Koken) with ten volumes of sterile phosphate buffer and stirring the mixture at 4° C. for 16 hours. Then, 40 µg of a ribonuclease (RNase A; SIGMA) was added to the prepared test solutions of GalNAc4S-6ST siRNA, and the mixtures were incubated to react at 37° C. The reaction time was 5, 15, 30, 45, or 60 minutes. 500 µl of RNA iso (Takara Bio) was added to the test solutions after reaction. The mixtures were incubated on ice for five minutes, and centrifuged at 14,000 rpm for 15 minutes. The resulting supernatants were collected, and 500 µl of isopropanol and 1 µl of glycogen (Invitrogen) were added thereto. The mixtures were incubated for 15 minutes, and centrifuged at 14,000 rpm for 15 minutes. The supernatants were discarded, and the pellets were saved. 1 ml of 75% ethanol was added to the pellets, and the mixtures were centrifuged at 14,000 rpm for 15 minutes. After this step was repeated twice, the pellets were dried and dissolved in 25 µl of injection solvent (Otsuka Pharmaceutical). 10 µl each of the solutions were combined with 2 µl of Loading Dye (Invitrogen). 3.5% agarose gel was prepared using UltraPure Agarose (Invitrogen), and the samples were electrophoresed in a Mupid-2 plus (ADVANCE) at 100 V for 20 minutes. After electrophoresis, the gel was shaken for 20 minutes in a stain solution prepared by 10,000 times diluting Ethidium Bromide (Invitrogen) with 1× LoTE (composition: 3 mM Tris-HCl (pH 7.5) (Invitrogen), 0.2 mM EDTA (pH 7.5) (Sigma Aldrich Japan)). The gel was photographed with Flu-ourchem (Innotech) and analyzed.

As seen in FIG. 6, in the absence of ribonuclease, GalNAc4S-6ST siRNA was relatively stable even after 60 minutes. However, in the presence of ribonuclease, siRNA degradation was observed at the time point after 15 minutes and the band disappeared after 30 minutes. On the other hand, when GalNAc4S-6ST siRNA was embedded in atelocollagen, the band was faint but detectable even after 30 minutes. Short-chain RNA (siRNA) embedded in atelocollagen has been reported to be resistant to ribonuclease. An equivalent result was obtained in this Example. Furthermore, the present invention also suggests that the same result is obtained not only when siRNA is embedded in atelocollagen but also in other biological substances having the same characteristics.

Example 7

Efficiency of Gene Knockdown by siRNA Administered into the Submucous Tissue of Large Intestine in Colitis Model Mice A colitis model mice was prepared by allowing C57BL/6J mice (female, six weeks old; CLEA Japan Inc.) to freely drink high-concentration chlorine water containing 3% dextran sulfate sodium (DSS; Wako Pure Chemical Industries Inc.) for five days. This DSS-induced colitis model has excellent reproducibility, and is thus used widely as a standard experimental model for inflammatory bowel diseases such as mouse ulcerative colitis and Crohn's disease (Sasaki N, J Inflamm. 2005 2: 13; as a review, Pucilowska J B et al. Am J Physiol Gastroenterol Liver Physiol. 279: G653-G659, 2000).

The same GalNAc4S-6ST siRNA (0.3 µg/head) as used in Example 5 was injected to the submucous tissue of mouse large intestine, while the mice were allowed to drink water containing 3% DSS. The control groups used were: a group injected with scramble siRNA ("BLOCK-iT Fluorescent Oligo (Invitrogen)" in Example 4) and an untreated group in which mice were allowed to drink DSS water only. The body weight and disease activity index (DAI) score (Kihara M, Gut. 2003 52: 713-9) were recorded for five days while the mice were allowed to drink water containing 3% DDS. Then, the mice were sacrificed on the fifth day.

1 ml of RNA iso (Takara Bio) was added to 50 mg each of excised organs (large intestine and kidney). The organs were crushed using an electrical homogenizer (DIGITAL HOMOGENIZER; AS ONE), then, 200 µl of chloroform (Sigma-Aldrich Japan) was added to the resulting suspension. The mixture was gently mixed and then cooled on ice for about five minutes, and centrifuged in a centrifuge (Centrifuge 5417R; Eppendorf) at 12,000 rpm and 4° C. for 15 minutes. After centrifugation, 500 µl of the supernatant was transferred to a fresh eppendorf tube, and an equal volume of isopropanol (500 µl; Sigma-Aldrich Japan) was added thereto. The solution was mixed, and then 1 µl of glycogen (Invitrogen) was added thereto. The mixture was cooled on ice for 15 minutes, and then centrifuged at 12,000 rpm and 4° C. for 15 minutes. Next, RNA precipitate obtained after washing three times with 1,000 µl of 75% ethanol (Sigma-Aldrich Japan) was air-dried for 30 minutes to one hour, and then dissolved in Otsuka distilled water (Otsuka Pharmaceutical Co., Ltd). The solution was 100 times diluted with Otsuka distilled water. The RNA concentrations of extracted samples in UV plates (Corning Costar) were determined using a plate reader (POWER Wave XS; BIO-TEK).

Next, reverse transcription reaction (cDNA synthesis) is conducted by the following procedure. The concentrations of the obtained RNA samples were adjusted to 500 ng/20 µl. The samples were heated at 68° C. for three minutes in a BLOCK INCUBATOR (ASTEC), and cooled on ice for ten minutes. After cooling on ice, 80 µl of RT PreMix solution (composition: 18.64 µl of 25 mM MgCl2 (Invitrogen), 20 µl of 5× Buffer (Invitrogen), 6.6 µl of 0.1 M DTT (Invitrogen), 10 µl of 10 mM dNTP mix (Invitrogen), 2 µl of RNase Inhibitor (Invitrogen), 1.2 µl of MMLV Reverse Transcriptase (Invitrogen), 2 µl of Random primer (Invitrogen), and 19.56 µl of sterile distilled water (Otsuka distilled water;

Otsuka Pharmaceutical Co., Ltd.)), which had been prepared in advance, was added to the samples. The mixtures were heated in a BLOCK INCUBATOR (ASTEC) at 42° C. for one hour and at 99° C. for five minutes, and then cooled on ice. 100 µl of desired cDNAs were prepared and quantitative PCR reaction was carried out using the prepared cDNAs in the following composition. For quantitative PCR, SYBR Premix Kit (TAKARA) and Real-time PCR thermal cycler DICE (TAKARA) were used. Conditions of PCR reaction was: 95° C. for 10 seconds, 40 cycles of 95° C. for 5 seconds and 60° C. for 30 seconds, finally, melting curve analysis was conducted. Nucleotide sequences of primers used in the quantitative PCR were described below.

[Quantitative PCR Primer Sequence]

```
*mouse GalNac4S-6ST (TAKARA)
forward:
                              (SEQ ID NO: 3)
5'-GTGAGTTCTGCTGCGGTCCA-3' reverse:
                              (SEQ ID NO: 4)
5'-AGTCCATGCTGATGCCCAGAG-3'

*mouse GAPDH (TAKARA)
Forward:
                              (SEQ ID NO: 5)
5'-CTGCCAAGTATGACATCA-3'

Reverse:
                              (SEQ ID NO: 6)
5'-TACTCCTTGGAGGCCATGTAG-3'
```

The results are shown in FIG. 7. The expression of GalNAc4S-6ST was significantly increased in the large intestine; however, the injected GalNAc4S-6ST siRNA significantly suppressed the increased expression. Meanwhile, in this model, the expression of GalNAc4S-6ST was not increased in the kidney, and remained unchanged even after injection of GalNAc4S-6ST siRNA. In addition, in the group injected with scramble siRNA, there was no significant change in the expression of GalNAc4S-6ST. Thus, the present invention demonstrated that GalNAc4S-6ST siRNA injected to the submucous tissue of large intestine was selectively retained in the large intestine. Furthermore, from the functional viewpoint, the GalNAc4S-6ST siRNA was demonstrated to significantly suppress the increase in the expression of GalNAc4S-6ST in the large intestine. The result described above suggests that the present invention is very effective for the retention and function of the injected physiologically active substances at the administration sites, and produces no side effect on other normal organs.

Example 8

Modification of Clinical/Pathological Features by Gene Knockdown Resulting from siRNA Administered to the Submucous Tissue of Large Intestine in Colitis Model Mice Since the retention and function of siRNA was demonstrated, its actual therapeutic effect was evaluated next. The colitis activity index (DAI) was analyzed by the same method described in Example 7.

The criteria for DAI evaluation are shown in Table 1 below.

TABLE 1

| INDEX | WEIGHT LOSS | STOOL CONSISTENCY | FECAL OCCULT BLOOD |
| --- | --- | --- | --- |
| 0 | NO | NORMAL | NORMAL |
| 1 | 1-5% |  | FECAL OCCULT BLOOD(+) |
| 2 | 5-10% | LOOSE STOOL | FECAL OCCULT BLOOD(++) |
| 3 | 10-20% |  | FECAL OCCULT BLOOD(+++) |
| 4 | >20% | DIARRHEA | SIGNIFICANT HEMORRHAGE |

The first day (day 0) of feeding with DSS water is defined as 1, and the stool consistency and fecal occult blood in each mouse were recorded. The results are shown in FIG. 8. As compared to the control group, the score was lower in the group administered with GalNAc4S-6ST siRNA. This result suggests that the GalNAc4S-6ST siRNA injected into the submucous tissue of large intestine suppresses the expression of GalNAc4S-6STgene in a colon-specific manner and exerted the effect of suppressing the inflammatory activity.

Example 9

Colonic-Contraction-Improving Effect of Gene Knockdown by siRNA Administered to the Submucous Tissue of Large Intestine in Colitis Model Mice Next, the length of the large intestine was measured after sacrificing mice on day five. Colonic contraction was significantly suppressed in the group administered with GalNAc4S-6ST siRNA ($p<0.05$; t test) (FIG. 9). The length of the large intestine is a crucial indicator that reflects the intestinal fibrosis. Thus, the GalNAc4S-6ST siRNA injected into the submucous tissue of large intestine was demonstrated to suppress the expression of GalNAc4S-6ST gene in a colon-specific manner. In addition, from the clinical viewpoint, the siRNA was demonstrated to strongly suppress fibrotic degeneration of the intestine.

Example 10

Histological Improvement Effect of Gene Knockdown by siRNA Administered to the Submucous Tissue of Large Intestine in Colitis Model Mice Next, tissue sections were prepared from collected large intestines and stained with hematoxylin-eosin. The resulting histological images were analyzed (FIG. 10). The epithelial disruption, infiltration of inflammatory cells into lamina propria and submucosa, and thickening of muscular layer were markedly suppressed in the group administered with GalNAc4S-6ST siRNA. Thus, the GalNAc4S-6ST siRNA injected into the submucous tissue of large intestine was demonstrated to suppress the expression of GalNAc4S-6ST gene in a colon-specific manner. In addition, the siRNA was also histologically demonstrated to produce a therapeutic effect.

The invention claimed is:

1. A method of treating an inflammatory bowel disease, comprising:
    directly injecting a formulation comprising siRNA into a target site of a submucous tissue of large intestine in a subject such that the siRNA suppresses expression of a targeted sequence,
    wherein the formulation comprises the siRNA in a naked form without any viral vector, and the siRNA comprises sequences of SEQ ID NO: 1 and SEQ ID NO: 2 and suppresses expression of GalNAc4S-6ST gene.

2. The method of claim 1, wherein the inflammatory bowel disease is ulcerative colitis.

3. The method of claim 1, wherein the inflammatory bowel disease is Crohn's disease.

4. The method of claim 1, wherein the directly injecting is carried out by an endoscope.

5. The method of claim 2, wherein the directly injecting is carried out by an endoscope.

6. The method of claim 3, wherein the directly injecting is carried out by an endoscope.

7. The method of claim 1, wherein the inflammatory bowel disease is one of ulcerative colitis and Crohn's disease.

8. The method of claim 7, wherein the directly injecting is carried out by an endoscope.

* * * * *